United States Patent [19]

Whistler

[11] 3,998,949
[45] Dec. 21, 1976

[54] MALE CONTRACEPTIVE

[75] Inventor: Roy L. Whistler, West Lafayette, Ind.

[73] Assignee: Purdue Research Foundation, West Lafayette, Ind.

[22] Filed: Mar. 13, 1975

[21] Appl. No.: 557,967

Related U.S. Application Data

[63] Continuation-in-part of Ser. No. 454,258, March 25, 1974.

[52] U.S. Cl. .............................. 424/180; 536/122
[51] Int. Cl.² ...................................... A61K 31/70
[58] Field of Search .................. 424/DIG. 14, 180

[56] References Cited
OTHER PUBLICATIONS

Chem. Abstracts, vol. 78, 1973, p. 261, paragraph 69506x.

*Primary Examiner*—Lewis Gotts
*Assistant Examiner*—Cary Owens
*Attorney, Agent, or Firm*—John R. Nesbitt

[57] ABSTRACT

A compound, namely 5-thio-D-glucose, and use thereof for a male contraceptive is disclosed herein. 5-Thio-D-glucose is administered periodically to inhibit development of sperm cells (spermatozoa). Sperm cells are arrested at the immature sperm cell level by administration of 5-thio-D-glucose, and this arrestment of cell development is maintained so long as administration of 5-thio-D-glucose is continued. After discontinuance of administration of 5-thio-D-glucose, however, the sperm cells again develop and normal sperm cell production is resumed.

10 Claims, No Drawings

MALE CONTRACEPTIVE

This application is a continuation-in-part of prior copending application Ser. No. 454,258, filed Mar. 25, 1974.

FIELD OF THE INVENTION

This invention relates to compound use as a male contraceptive and more particularly relates to the use of 5-thio-D-glucose for inhibiting development of spermatozoa.

BACKGROUND OF THE INVENTION

In the medical field, much effort has been devoted to preventing undesired pregnancy of a female. While various methods and compounds have been developed for administration and/or use by females in preventing unwanted pregnancies, no contraceptive compound has heretofore been developed suitable for administration to males to safely and satisfactorily inhibit development of sperm cells.

A few years ago, a novel sulfur-containing compound and method for the preparation of the same was described and claimed in U.S. Pat. No. 3,243,425. The sulfur compounds of that invention are based upon the replacement of an oxygen atom in a sugar molecule by a sulfur atom, and, more specifically, are based upon the replacement of the ring oxygen of the sugar by the sulfur atom and oxidized forms of the sulfur atom and thus may be described as thio-sugars.

While the compounds described in U.S. Pat. No. 3,243,425 were then recognized to be of both chemical and biochemical interest as sugar analogs, the then recognized use of the compounds was primarily in the preparation of resins by reaction with a diisocyanate or other polyisocyanates, with usefulness as radiation absorbers and as chain terminators in free radical polymerizations being mentioned. 5-Thio-D-glucose has also been found useful as a tumor cell growth restructing compound and as a weight control compound. Patent applications directed to such compound uses have been made the subject matter of U.S. patent applications filed on Feb. 14, 1974 and given Ser. Nos. 442,448 and 442,447, respectively. It has remained until now, however, to find and develop usefulness for 5-thio-D-glucose as a male contraceptive.

SUMMARY OF THE INVENTION

This invention provides a compound useful as a male contraceptive. 5-Thio-D-glucose is utilized to inhibit and stop sperm cell maturation in a male, with arrestment of sperm development being maintained only while the administration of 5-thio-D-glucose is continued, and normal spermatazoa production being resumed shortly after termination of administration of such compound.

It is therefore an object of this invention to provide a novel compound use as a male contraceptive.

It is another object of this invention to provide 5-thio-D-glucose and administer the same to a recipient to inhibit the development of sperm cells in a male.

It is still another object of this invention to provide 5-thio-D-glucose and administer the same periodically to prevent maturation of sperm cells.

It is yet another object of this invention to provide 5-thio-D-glucose so that maturation of sperm cells is prevented only while administration of 5-thio-D-glucose is continued.

It is still another object of this invention to provide 5-thio-D-glucose initially at one dosage level and then to thereafter provide 5-thio-D-glucose initially at one dosage level and then to thereafter provide 5-thio-D-glucose at a lower dosage level to thus prevent maturation of sperm cells on a continuing basis.

It is yet another object of this invention to provide a method for inhibiting development of sperm cells by administering 5-thio-D-glucose.

With these and other objects in view which will become obvious to one skilled in the art as the description proceeds, this invention resides in the novel compound use substantially as hereinafter described and more particularly defined by the appended claims, it being understood that such changes in the precise embodiment and use of the herein disclosed invention are meant to be included as come within the scope of the claims.

DESCRIPTION OF THE INVENTION

It has been found that 5-thio-D-glucose can be used as a male contraceptive. 5-Thio-D-glucose is the nearest analog of real D-glucose, a common sugar in the diet and sometimes called blood sugar.

The structural formula for 5-thio-D-glucose is as follows:

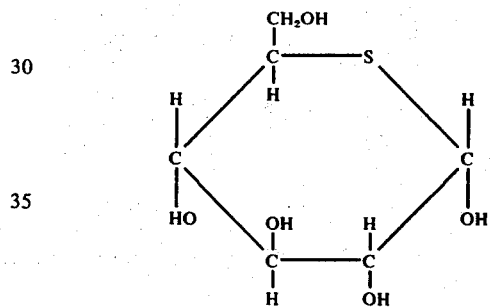

It has been found that 5-thio-D-glucose, when administered in predetermined doses, prevents development or maturation of sperm cells (spermatozoa) in normal mammalian subjects capable of sperm formation; and so long as a predetermined minimum dosage of 5-thio-D-glucose is administered, after initial development of sperm cells is terminated, such sperm cells are prevented from developing on a continuing basis. It has also been found that shortly after discontinuance of administration of 5-thio-D-glucose, normal development of spermatozoa resumes and the male animal is thereafter able to procreate in normal fashion.

5-Thio-D-glucose has been shown to have very low toxicity as it has been found that the $LD_{50}$ (i.e. the lethal dosage required to kill half of the animals tested) is in the neighborhood of 14,000 mg/kg of body weight of the animal. Since other compounds also having $LD_{50}$ in this neighborhood are considered completely innocuous, it can easily be appreciated that 5-thio-D-glucose is considered to be essentially non-toxic to intact animals.

In tests to date utilizing different groups of male mice, administration of 5-thio-D-glucose showed that dose levels extending over the range of from about 5 mg. through 200 mg/kg/day caused an inhibition and stoppage of maturation of sperm cells (properly termed spermatozoa). In other words, it has been found that administering 5-thio-D-glucose in the range of 5 mg. to 200 mg. per kg. of animal weight per day was sufficient to inhibit and stop maturation of sperm cells. It has been found, however, that the onset of the desired effect is more rapid when 5-thio-D-glucose is administered in larger dosages. However, in all cases, development of spermatozoa was arrested at the immature cell level and possibly at the immature spermatogonium or spermatocyte level when administered in a dosage level of at least 33.1 mg/kg/day. A histological examination of the testes of the males administered 5-thio-D-glucose at levels equal to or exceeding 33.1 mg/kg/day showed that the sperm generating cells had been arrested at the immature sperm cell level and that the arrestment was maintained for so long as use of the drug was continued, even though the dosage level was reduced as low as about 5 mg/kg/day. It has likewise been observed that it should be unnecessary to administer 5-thio-D-glucose daily, but only periodically with administration possibly not more often than once or twice a week being needed to continue complete inhibition and stopping of maturation of the sperm cells. It was found as a result of testing that even after a two month period, arrestment of sperm cell maturation was maintained so long as administration of 5-thio-D-glucose was continued at a minimum dosage level of about 5/mg/kg/day.

However, it was also shown that after administration of 5-thio-D-glucose was discontinued, the sperm cells began to develop in a normal manner and came to maturation within a short time thereafter. With male mice, it was found that within weeks of withdrawal of 5-thio-D-glucose, the male mice were able to normally fertilize females and produce normal offspring. A histological examination of the testes of the male mice after withdrawal of 5-thio-D-glucose showed normal spermatozoa production with the entire tissue appearing to be normal.

With specific reference to the experiments conducted on male mice, the results of the experiments are shown in Table I as follows:

TABLE I

Sperm Inhibition by 5-thio-D-glucose

TABLE I

| Sperm Inhibition by 5-thio-D-glucose | | | | | |
|---|---|---|---|---|---|
| 5-thio-D-glucose mg/kg/day | 0 | 13.7 | 33.1 | 74.4 | 200 |
| Sperm production after 2 months | Normal | Normal | -0- | -0- | -0- |

The initial experiment on male mice is shown at the right side of Table I, wherein male mice were administered 200 mg/kg/day of 5-thio-D-glucose by oral administration, that is, the 5-thio-D-glucose was mixed in the animal feed. The result, as shown in Table I, was that the male mice lost the ability to produce sperm cells. This loss of sperm production was proven by histological examination of the testes tissue. However, after the male mice in the initial test had been given 5-thio-D-glucose at a dosage level of 200 mg/kg/day for a period of two months, administration of 5-thio-D-glucose was discontinued, and it was found that within a period of two months thereafter, the testes tissue had returned to normal as again evidenced by histological examination.

In a further test as shown in Table I, four groups of male mice were utilized. A first group was used as a control group and was not administered 5-thio-D-glucose, while the other three groups were administered different dosage levels of 5-thio-D-glucose, with a second group receiving 13.7 mg/kg/day, a third group receiving 33.1 mg/kg/day, and the fourth group receiving 74.4 mg/kg/day. The groups receiving the 5-thio-D-glucose were administered the same for a period of two month period, histological examination of the tissue sections taken from the testes was again conducted, and these tests showed that the first and second groups (receiving 0 and 13.7 mg/kg/day, respectively, of 5-thio-D-glucose) had normal sperm production, while the third and fourth groups (receiving 33.1 and 74.4 mg/kg/day, respectively, of 5-thio-D-glucose) were found to be producing no sperm.

Following the two months of administration of 5-thio-D-glucose to the test animals, administration of the compound was discontinued for a period of two weeks. After two weeks, tissue sections were taken from the testes of some of the male mice in each of the four groups, and it was observed that the male mice in the first two groups (receiving 0 and 13.7 mg/kg/day, respectively, of 5-thio-D-glucose) were continuing to produce normal quantities of sperm, while the third and fourth groups receiving the larger dosages (33.1 and 74.4 mg/kg/day) continued to have no sperm production. However, after a period of two months following discontinuance of administration of 5-thio-D-glucose to the male mice, further histological examinations confirmed that all groups showed normal sperm production. At this time, male mice from each group when mated with normal females were found to be able to cause production of normal litters.

In a further test, a group of male mice was administered 33 mg/kg/day of 5-thio-D-glucose for a period of one month. At this time, it was found that the male mice has lost the ability to produce sperm. At that time, the dosage of 5-thio-D-glucose was reduced to 40 mg/kg of 5-thio-D-glucose per week, and the mice were found thereafter, by periodic examination, to produce no sperm on a continuing basis. Thus, after sperm generation is stopped by a substantial dosage of 5-thio-D-glucose, continuance of periodic administration of 5-thio-D-glucose at lower dosage levels is shown to be sufficient to prevent sperm production.

The foregoing tests and experiments indicate that 5-thio-D-glucose, when administered orally to male mice at an appropriate dose level, brings about complete inhibition of sperm production, and that after an appropriate period following drug removal, normal sperm production recurs, and the animals are thereafter able to procreate in a normal fashion. It has also been found, however, that so long as administration of 5-thio-D-glucose is continued, even at lower dosage levels, complete inhibition of sperm production is maintained until discontinuance of administration of 5-thio-D-glucose.

Effective inhibitory dosage requirements might vary, of course, and would be expected to vary in different animals, and thus it is to be expected that a lower or higher daily dose intake might be required, depending upon the specific male recipient. Likewise, while the tests indicate that after inhibition of sperm production there is a period of time after withdrawal of 5-thio-D-glucose before normal sperm production is reinitiated, such normal sperm production does occur without apparent adverse effect on the ability of the male to procreate. Since it does take some time for sperm production to resume, however, continuing inhibition of sperm production can be achieved by periodic administration of 5-thio-D-glucose as would be necessary to prevent the reinitiation of sperm production and could, for example, be weekly or monthly in a single dosage.

From the foregoing, it is to be realized that the compound use as brought out in this invention provides an effective male contraceptive.

Accordingly, there is provided a method for inhibiting development of sperm cells which comprises administering to a male mammalian recipient capable of producing sperm at least an effective amount of 5-thio-D-glucose over a period of time during which such inhibition is required.

A further embodiment is the method for inhibiting development of sperm cells which comprise administering to a male mammalian recipient capable of producing sperm an initial dose at least large enough and for a time period sufficient to bring about aspermatogenesis and thereafter administering a smaller maintenance dose over a period of time during which inhibition of spermatogenesis is desired.

The dose rate for producing initial aspermatogenesis is from about 30 mg/kg to 200 mg/kg on a daily dose basis. Larger doses would be required if the interval between doses were increased. The maintenance dose can be as low as 5 mg/kg per day. It will be recognized that the dose required may vary as between species of mammals, and there may also be variation in the response of individuals, requiring adjustment of the dosage rates.

5-Thio-D-glucose is very soluble in water and has an agreeably sweet taste. For administration to the male mammalian recipients the compound can be administered in any of the usual pharmaceutical dosage forms. Thus, tablets, capsules, suspensions or solutions can be made to contain the dosage forms. Tablets are made incorporating the 5thio-D-glucose in the selected individual dosage. Conveniently, tablets containing of the order of 50 mg. to 2 grams per tablet are made. The drug is admixed with a suitable excipient or diluent if required and with a binder and then pressed into tablets. Useful as binders, diluents, fillers or excipients are any of the materials well known for such purposes, e.g. starch, gelatin, lactose, talc, stearic acid, gum acacia and the like. Alternatively, the 5-thio-D-glucose in admixture with a diluent or excipient can be filled into gelatin capsules.

Desirably, the 5-thio-D-glucose is administered for the purpose of this invention in a formulation which is effective to prolong the duration of action of the drug in the body. Because the drug is so soluble, it is normally quickly absorbed and then excreted. Use of tablets or capsules which incorporate agents to delay or retard the absorption rate is thus a preferred form of administration. Incorporation of the 5-thio-D-glucose into polymer matrices or formation of small particles having different solubility rates in the manner known to the art which are then placed in telescoping gelatin capsules, are exemplary of such dose formulations.

For administration parenterally, 1 to 10 percent sterile solutions of 5-thio-D-glucose in water can be made. Other liquid formulations, for oral administration, can be the usual pharmaceutical elixirs or syrups with a suitable concentration of the drug to provide the selected dose in a convenient single dose amount, e.g. 50 mg. to 2 grams in 5 to 10 ml. of the liquid.

Administration to animals is practically and conveniently accomplished by mixing the 5-thio-D-glucose into the feed.

What is claimed is:

1. A method for inhibiting development of sperm cells which comprises orally or parenterally administering to a male mammalian recipient capable of producing sperm at least an effective amount of 5-Thio-D-glucose over a period of time during which such inhibition is required.

2. The method according to claim 1 wherein a sufficient amount of 5-thio-D-glucose is administered to stop maturation of sperm cells.

3. The method of claim 1 wherein said 5-thio-D-glucose is administered periodically in regular sequential doses.

4. The method of claim 3 wherein said 5-Thio-D-glucose is orally administered in periodic dosages ranging from about 33 mg/kg/day to 200 mg/kg/day.

5. The method of claim 1 wherein after termination of administration of said 5-thio-D-glucose normal development of sperm cells is resumed.

6. A pharmaceutical preparation useful as a male antifertility agent comprising 5-thio-D-glucose in a pharmaceutically acceptable dosage form.

7. A method for inhibiting development of sperm cells, said method comprising orally administering to a male mammalian recipient capable of producing sperm at least about 30 mg/kg/day of 5-Thio-D-glucose as an initial dose rate for a time sufficient to bring about inhibition of development of sperm cells and then administering a substantially smaller maintenance dose rate of said compound over a period of time during which such inhibition is required.

8. The method of claim 7 wherein after termination of administration of said maintenance dosage 5-thio-D-glucose normal development of sperm cells is resumed.

9. A method according to claim 7 wherein the said initial dosage form and said maintenance dosage form comprise 5-thio-D-glucose in a pharmaceutically acceptable dosage form.

10. A pharmaceutical composition useful in the process of claim 7 as a male antifertility agent comprising 5thio-D-glucose dispersed in a pharmaceutical extending medium adapted for use as a dosage form in amount such that when taken in single dose it is a maintenance dose and when taken in form three- to five-fold dose it is an initial dose.

* * * * *